(12) United States Patent
Butterfield (10) Patent No.: US 8,585,649 B2
(45) Date of Patent: Nov. 19, 2013

(54) TUBULAR PUMPING ELEMENT

(75) Inventor: Robert D. Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 406 days.

(21) Appl. No.: 12/970,809

(22) Filed: Dec. 16, 2010

(65) Prior Publication Data
US 2012/0157919 A1   Jun. 21, 2012

(51) Int. Cl.
*A61M 1/00* (2006.01)
(52) U.S. Cl.
USPC ........................................................ 604/153
(58) Field of Classification Search
USPC .......... 604/131–155, 244–262, 93.01, 19, 27, 604/36; 417/375, 389, 412
See application file for complete search history.

(56) References Cited

U.S. PATENT DOCUMENTS

| 4,558,989 A | 12/1985 | Chappell |
| 6,213,739 B1 | 4/2001 | Phallen et al. |
| 7,396,351 B2 * | 7/2008 | Freyman et al. ............... 604/537 |
| 2006/0173412 A1 | 8/2006 | Susi |
| 2007/0093910 A1 * | 4/2007 | Imran ......................... 623/23.65 |

FOREIGN PATENT DOCUMENTS

EP      0215249      3/1987

OTHER PUBLICATIONS

International Search Report and Written Opinion for International Application No. PCT/US2011/064473 mailed Jun. 29, 2012.

* cited by examiner

*Primary Examiner* — Matthew F Desanto
(74) *Attorney, Agent, or Firm* — McDermott Will & Emery LLP (57) ABSTRACT

A tubular pumping element for pumping a liquid is disclosed. The tubular pumping element includes an outer shell that has a bore with an inlet and an outlet at opposite ends of the bore. There is a flow path for the liquid from the inlet through the bore to the outlet. A support element is located within the bore of the outer shell. An elastic sleeve is located over the support element and has a plurality of expandable portions. The support element includes a plurality of fluid passages each coupled to a respective port on the surface of the support element under one of the plurality of expandable portions of the elastic sleeve. Introduction of a driving fluid into one of the fluid passages causes the expandable portion of the elastic sleeve that is proximate to the respective port to expand.

27 Claims, 9 Drawing Sheets

FIG. 11

TUBULAR PUMPING ELEMENT

BACKGROUND

1. Field

The present disclosure generally relates to the administration of medication by infusion and, more particularly, to an infusion pumping element.

2. Description of the Related Art

Many individuals suffer from chronic health problems, the treatment of which requires regular, and sometimes extended, medication deliveries. Certain treatment regimens for diseases such as diabetes, asthma, epilepsy, cancer and even allergies, require the regular delivery of precise amounts of medication for the patient's survival. Treating chronic medical disorders often requires the administration of medication over a long period of time according to a treatment regimen specified by a medical professional, such as a physician.

In cases of patients admitted to a healthcare facility, one or more infusions to be administered to a patient are prescribed by the patient's physician. A pharmacy, generally located within the patient's hospital or healthcare facility, prepares the infusion medication or solution according to the physician's prescription. The pharmacist places the infusion solution in a bag, bottle, syringe, or other container and labels the container. The label typically contains data to identify the patient, physician, medication prescribed, and a control number. The label is generally typed or printed in human readable characters and may also include machine-readable information, such as a bar code that is readable by optical energy or a radio frequency identification (RFID) tag that is readable by radio frequency (RF) energy. The container is transported to the patient's location and a clinician such as a nurse or other health practitioner hangs the container from a rack. The nurse connects a tube between the container and an infusion pumping system and inserts a cannula at the end of the tube into a vein, for an intravenous (IV) infusion, or other part of a patient. The tube may be part of an assembly that includes fittings, connectors, and pumping elements and is frequently referred to as an "IV set." The pump of the infusion pumping system is started and the infusion proceeds.

Existing infusion pumps include peristaltic pumps that sequentially compress and release segments of an elastic line as well as pumps that manipulate pumping chambers that are incorporated into the IV set. The accuracy of a peristaltic pump is affected by the inner diameter of the tubing using in the IV set and elastic tubing having a precise inner diameter is more difficult to produce and therefore more expensive. Similarly, the accuracy of an infusion pump that uses a pumping chamber is dependent upon the accuracy of the size and resilience of the pumping chamber, again leading to a need to produce the disposable IV set in quantities of millions with high accuracy.

The infusion pumps that utilize the peristaltic tubes and elastic pumping elements described above are frequently complex systems with numerous moving parts to properly manipulate the matching pumping element. The sequential actuation required to precisely control displacement of the pumping element may require expensive motor controllers or complex mechanical linkages. In addition to the impact of this complexity on reliability and cost of the infusion pump, operation of this type of mechanism is frequently noisy. As infusion pumps are commonly used on a continuous basis, both within a healthcare facility and in other environments such as a patient's home, the noise can be a distraction and, in some cases, interfere with the patient's sleep, further affecting their recovery.

Providing an infusion pump that is able to deliver fluid at an accurate flow rate using a low-cost IV set would provide an advantage. Providing an infusion pump that accomplishes this while also being more reliable, less expensive, and/or quieter than current infusion pumps would be an additional advantage.

SUMMARY

The pumping element of the present disclosure provides precise delivery of fluid and is simple to produce. The disclosed infusion pump is smaller, more reliable, and quieter than certain existing infusion pumps.

A pumping element for pumping a medical fluid is disclosed. The pumping element comprises an outer cylinder comprising a tube having a bore with a first end, a second end, and an internal wall, an inlet coupled to the first end, an outlet coupled to the second end, and a flow path for the medical fluid from the inlet through the bore to the outlet, a support element located at least partially within the bore of the outer cylinder, the support element comprising a first end and an external surface having a plurality of ports spaced along the external surface, a coupler attached to the first end of the support element, the coupler having a plurality of driving fluid connectors, and an elastic sleeve coupled to the external surface of the support element, the elastic sleeve comprising a plurality of expandable portions spaced along the elastic sleeve, each expandable portion proximate to one of the ports, wherein the support element further comprises a plurality of separate fluid passages each coupled between one of the plurality of ports and one of the plurality of driving fluid connectors, and wherein introduction of a driving fluid into one of the driving fluid connectors of the coupler causes the expandable portion of the elastic sleeve that is proximate to the port coupled to the driving fluid connector to expand until the elastic sleeve contacts the internal wall of the outer cylinder and blocks the flow path of the medical fluid through the outer cylinder.

An IV set for use with an infusion pump to deliver fluid from a source of medical fluid to a patient is disclosed. The IV set comprises an outer cylinder comprising a tube having a bore with a first end, a second end, and an internal wall, an inlet coupled to the first end, an outlet coupled to the second end, and a flow path of the medical fluid from the inlet through the bore to the outlet, a support element located at least partially within the bore of the outer cylinder, the support element comprising a first end and an external surface having a plurality of ports spaced along the external surface, a coupler attached to the first end of the support element, the coupler having a plurality of driving fluid connectors, and an elastic sleeve coupled to the external surface of the support element, the elastic sleeve comprising a plurality of expandable portions spaced along the elastic sleeve, each expandable portion proximate to one of the ports, wherein the support element further comprises a plurality of separate fluid passages each coupled between one of the plurality of ports and one of the plurality of driving fluid connectors, and wherein introduction of a driving fluid into one of the driving fluid connectors of the coupler causes the expandable portion of the elastic sleeve that is proximate to the port coupled to the driving fluid connector to expand until the elastic sleeve contacts the internal wall of the outer cylinder and blocks the flow path of the outer cylinder, a first tube having first and second ends, the first end coupled to the inlet of the outer cylinder, the second end configured to couple to the source of medical fluid, and a second tube having first and second ends, the first end coupled to the outlet of the outer cylinder, the second end configured to couple to a cannula that is configured to introduce fluid into the body of the patient.

An infusion pump system for delivery of fluid from a source of medical fluid to a patient is disclosed. The system comprises an IV set that comprises an outer cylinder comprising a tube having a bore with a first end, a second end, and an internal wall, an inlet coupled to the first end, an outlet coupled to the second end, and a fluid path for the medical fluid from the inlet through the bore to the outlet, a support element located at least partially within the bore of the outer cylinder, the support element comprising a first end and an external surface having a plurality of ports spaced along the external surface, a coupler attached to the first end of the support element, the coupler having a plurality of driving fluid connectors, and an elastic sleeve coupled to the external surface of the support element, the elastic sleeve comprising a plurality of expandable portions spaced along the elastic sleeve, each expandable portion proximate to one of the ports, wherein the support element further comprises a plurality of separate fluid passages each coupled between one of the plurality of ports and one of the plurality of driving fluid connectors, and wherein introduction of a driving fluid into one of the driving fluid connectors of the coupler causes the expandable portion of the elastic sleeve that is proximate to the port coupled to the driving fluid connector to expand until the elastic sleeve contacts the internal wall of the outer cylinder and blocks the flow path of the outer cylinder, a first tube having first and second ends, the first end coupled to the inlet of the outer cylinder, the second end configured to couple to the source of medical fluid, and a second tube having first and second ends, the first end coupled to the outlet of the outer cylinder, the second end configured to couple to a cannula that is configured to introduce fluid into the body of the patient, and an infusion pump comprising at least one source of the driving fluid, a plurality of valve elements each coupled between the at least one source of driving fluid and one of the plurality of driving fluid connectors of the coupler, each valve element configured to selectively couple the driving fluid connector to the source of driving fluid, wherein the valve elements are activated so as to intermittently direct the driving fluid expand and collapse the portions of the elastic sleeve in a sequence that causes fluid to flow from the inlet to the outlet.

DETAILED DESCRIPTION

The disclosed embodiments of a pumping element, an IV set, and an IV pumping system provide a quiet, reliable method of delivering a fluid at a precise rate using low-cost disposable IV sets.

The embodiments of the methods and systems disclosed herein are presented in the context of an infusion pump for the delivery of medical fluid to a patient. It will be apparent to those of ordinary skill in the art that the disclosed concepts may be applied to a variety of mechanisms for the pumping of liquids. Nothing in this disclosure should be interpreted, unless specifically stated as such, to limit the application of any method or system disclosed herein to medical applications.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
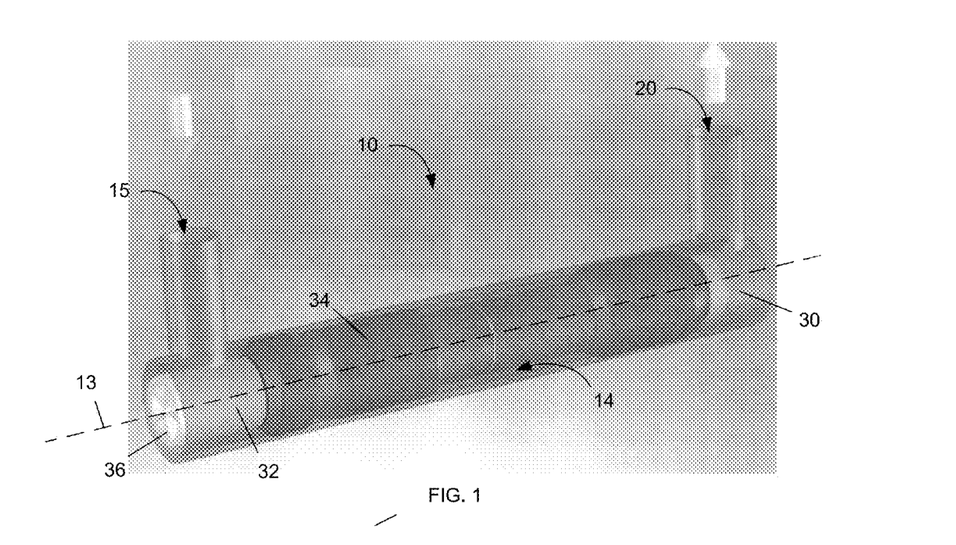
FIG. 1 is a perspective view of a tubular pumping element according to certain aspects of the disclosure.

FIG. 1 is a perspective view of a tubular pumping element 10 according to certain aspects of the disclosure. The embodiment shown in FIG. 1 has a tubular outer shell 30 that is sealed at both ends. An inlet 15 and an outlet 20 are provided at opposite ends and, in FIG. 1, extend perpendicular the central axis 13 of the tubular pumping element 10. Outer shell 30 is shown as transparent in FIG. 1 to reveal the inner components of the tubular pumping element 10. Inside the bore 14 of outer shell 30 is a tubular support element 32 with a coupling 36 at one end that protrudes through the outer shell 30. An elastic sleeve 34 covers a portion of the support element 32. The details of the construction and operation of the tubular pumping element 10 are described in more detail in relation to later figures.

Figure 2:
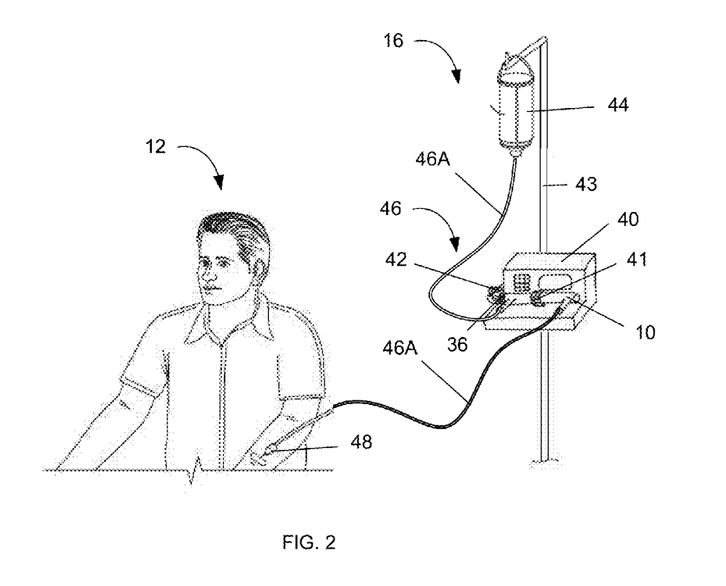
FIG. 2 depicts a patient receiving an infusion of medical fluid through a pumping system 16 that includes an intravenous (IV) set with a tubular pumping element coupled to an IV pump according to certain aspects of the disclosure.

FIG. 2 depicts a patient 12 receiving an infusion of medical fluid through a pumping system 16 that includes an IV set 46 with a tubular pumping element 10 coupled to an IV pump 40 according to certain aspects of the disclosure. The tubular pumping element 10 is mechanically secured to the IV pump 40 with a clamp 41. A set of driving fluid tubes 42 is coupled to the coupling 36. The IV set 46 includes lengths of tubing 46A having fittings (not shown) that connect to a medical fluid container 44 at one end and to an infusion device 48, such as an intravenous cannula, at the other end. In certain embodiments, the tubular pumping element 10 is provided as part of the IV set 46. In certain embodiments, the tubular pumping element 10 is provided as a separate unit that connects to the IV set 46. In the embodiment of FIG. 2, the IV pump 40 is mounted on a pole 43 for convenient movement with the patient 12 about a healthcare facility. In certain embodiments, the IV pump 40 is a stand-alone unit. In certain embodiments, the tubular pumping element 10 is not mechanically secured to the IV pump 40. In certain embodiments, the IV pump 40 is a portable unit carried by the patient 12.

Figure 3A:
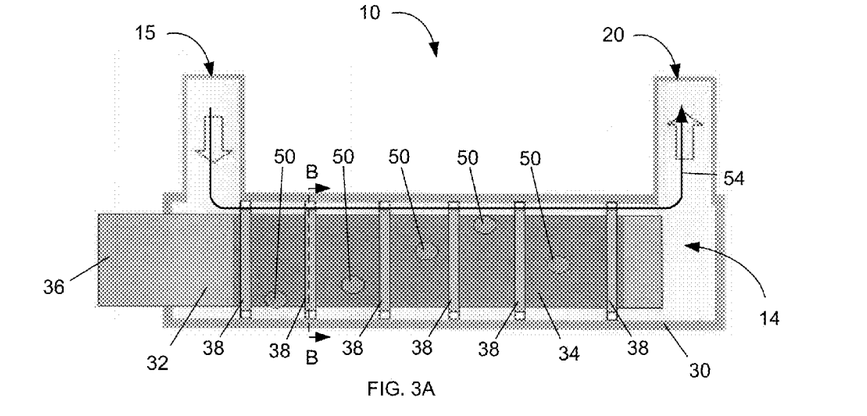
FIGS. 3A-3B are cross-sections of the pumping element of FIG. 1 according to certain aspects of the disclosure.
Figure 3B:
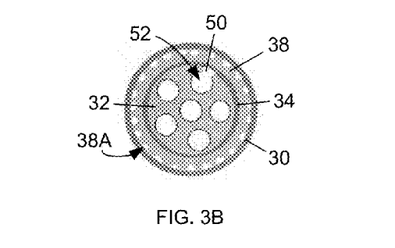

FIGS. 3A-3B are cross-sections of the tubular pumping element 10 of FIG. 1 according to certain aspects of the disclosure. FIG. 3A is a cross-section along the centerline 13 of the tubular pumping element 10. The elastic sleeve 34 is shown over a portion of support element 32. A plurality of ports 50 on the surface of the support element 32 are shown here although these ports 50 are under the elastic sleeve 34. There are a plurality of spacers 38 that position the support element 32 and elastic sleeve 34 within the bore 14 of outer shell 30. It can be seen in FIG. 3A that coupler 36 of the support element 32 protrudes through the outer shell 30. There is a flow path 54 from the inlet 15 through the bore 14 to the outlet 20, wherein the fluid flows between the internal wall of outer shell 30 and the elastic sleeve 34. In certain embodiments, spacers 38 are placed at only a few of the locations 38. In certain embodiments, only two spacers 38 are used in the tubular pumping element 10.

FIG. 3B is a cross-section of the entire tubular pumping element 10 taken along the line B-B shown in FIG. 3A. It can be seen that the elastic sleeve 34 is over the support element 32 and that the support element 32 has a plurality of internal passages 52 that each connect at one end of the respective passage 52 to one of the ports 50 on the surface of support element 32. Each of the internal passages 52 terminates at its other respective end to a driving fluid connector (not shown in FIGS. 3A and 3B) on the coupler 36. It can also be seen how the spacers 38 position the support element 32 and elastic sleeve 34 within outer shell 30 and have, in this embodiment, a plurality of notches 38A around the outer edge that allow flow past the spacers 38.

Figure 4:
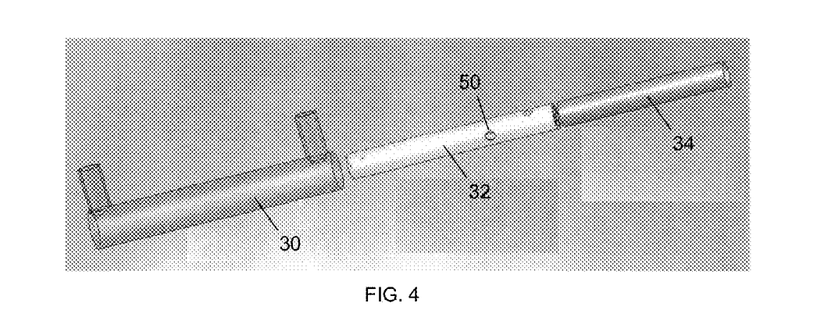
FIG. 4 is an exploded view of certain components of the tubular pumping element according to certain aspects of the disclosure.

FIG. 4 is an exploded view of certain components of the tubular pumping element 10 according to certain aspects of the disclosure. Sleeve 34 fits over support element 32 which then together are positioned within the outer shell 30. Some of the ports 50 are visible on the surface of support element 32.

Figure 5:
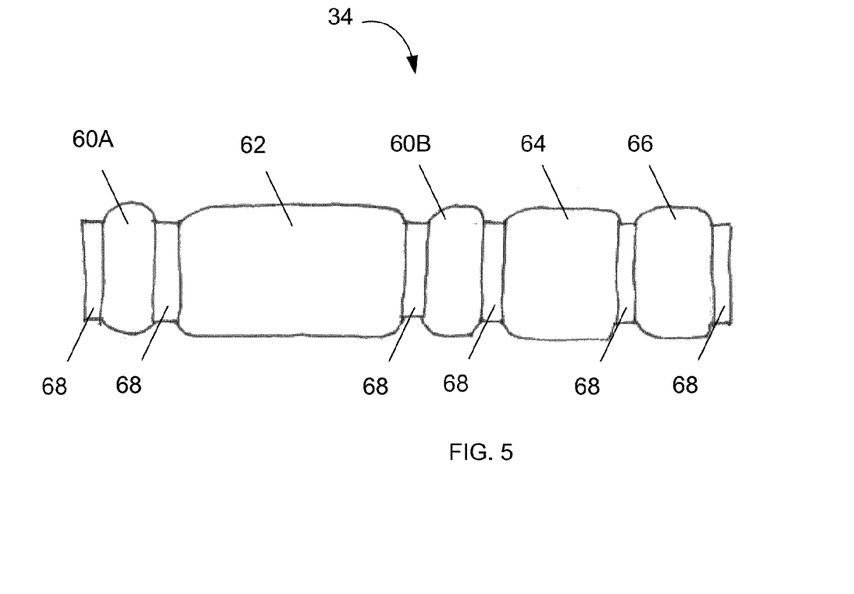
FIG. 5 depicts an elastic sleeve configured with shorter valve portions and a longer pumping portion according to certain aspects of the disclosure.

FIG. 5 depicts an elastic sleeve 34 configured with shorter valve portions 60A, 60B and a longer pumping portion 62 according to certain aspects of the disclosure. In the embodiment of FIG. 5, the elastic sleeve 34 is circumferentially sealed to the support element (not shown) at locations 68. The portions of the elastic sleeve 34 between adjacent locations 68 define pumping portion 62, valves 60A and 60B, compensator 64, and damper 66. The operation of these elements is described later relative to FIGS. 10A-10F.

Figure 6:
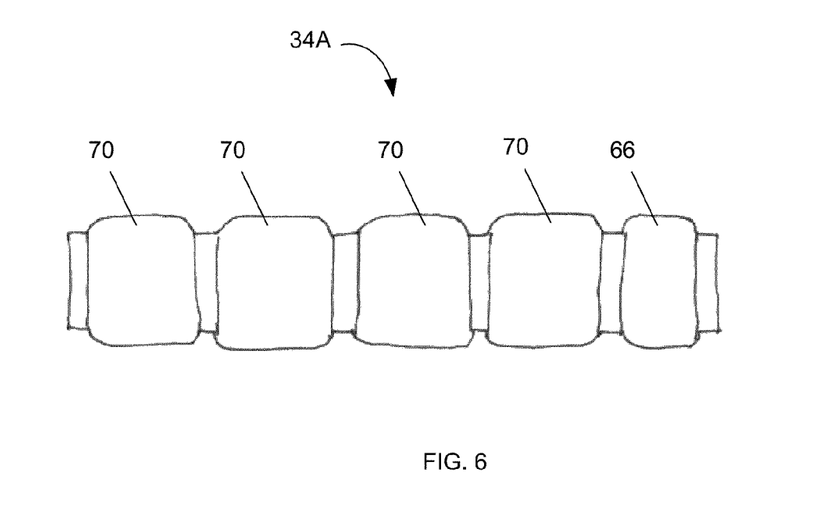
FIG. 6 depicts an elastic sleeve configured with uniform pumping portions according to certain aspects of the disclosure.

FIG. 6 depicts an elastic sleeve 34A configured with uniform pumping portions 70 according to certain aspects of the disclosure. In this embodiment, the four pumping portions 70 are sequentially expanded and contracted in a peristaltic fashion to pump fluid.

Figure 7A:
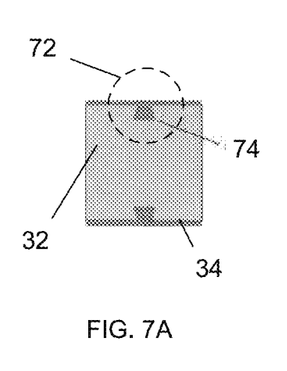
FIGS. 7A-7B depict an elastic sleeve having an interlocking feature according to certain aspects of the disclosure.
Figure 7B:
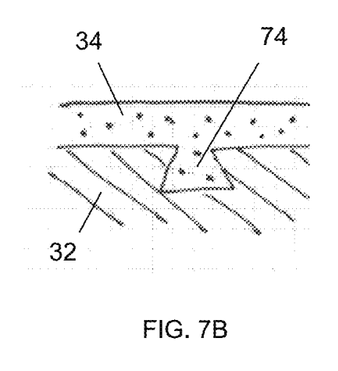

FIGS. 7A-7B depict an elastic sleeve 24 having an interlocking feature 74 that secures the elastic sleeve 34 to the support element 32 and seals between adjacent portions according to certain aspects of the disclosure. The interlocking feature 74, in this embodiment, is a reverse tapered wedge around the inner circumference of the elastic sleeve 34 that fits into a circumferential notch of the support element 32 that has a matching profile. The reverse taper of the interlocking feature 74 both mechanically locks and seals the elastic sleeve 34 to the support element 32. FIG. 7B is a close-up of the interlocking feature 74.

Figure 8:
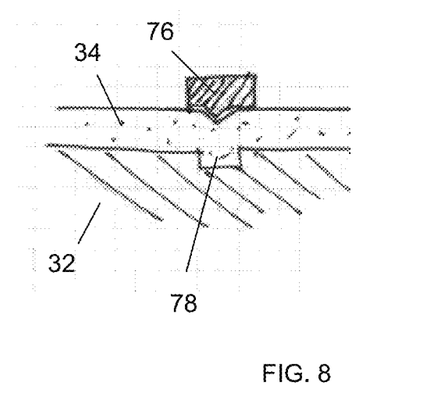
FIG. 8 depicts an elastic sleeve secured to a support element according to certain aspects of the disclosure.

FIG. 8 depicts an embodiment of the tubular pumping element 10 where a separate clamp ring 76 is placed around the elastic sleeve 34 to clamp the elastic sleeve 34 to the support element 32. In this embodiment, the elastic sleeve 34 has a locating ridge 78 around the inner circumference that fits into a matching circumferential notch in the support element 32. In certain embodiments, the elastic sleeve 34 has locating features that are not circumferential such as raised bumps or posts that fit into matching features of the support element 32. In certain embodiments, there are no locating features in either the elastic sleeve 34 or the support element 32 and clamps 76 are placed at specified locations to seal the elastic sleeve 34 to the support element 32.

Figure 9A:
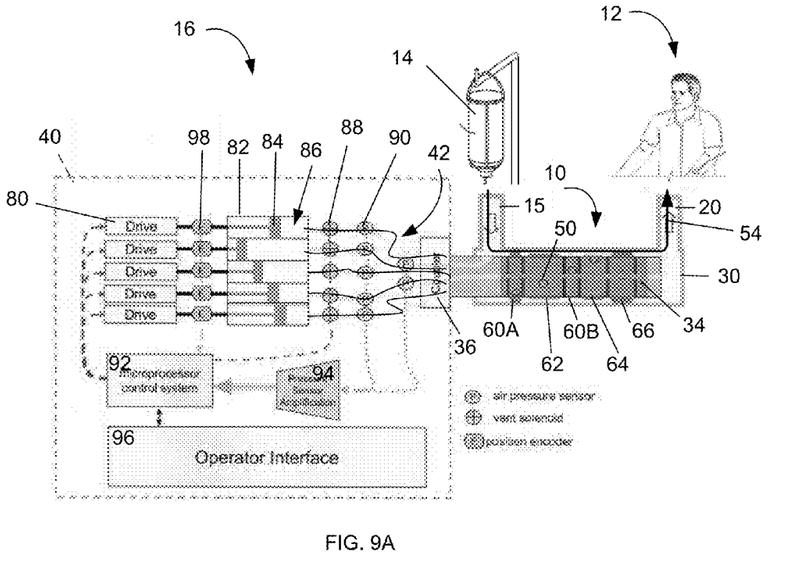
FIG. 9A is a schematic of a displacement-driven pumping system according to certain aspects of the disclosure.

FIG. 9A is a schematic of a displacement-driven pumping system 16 according to certain aspects of the disclosure. The pumping system 16 includes an IV pump 40 that is connected through driving fluid tubes 42 to connectors (not shown) on coupler 36 of tubular pumping element 10. The inlet 15 is coupled to a container 14 of medical fluid and the outlet 20 is coupled to a patient 12 by an IV set 46 (not shown in FIG. 9A) of the type shown in FIG. 2 and wherein the tubular pumping element 10 is a part of the IV set 46.

In the embodiment of FIG. 9A, the IV pump 40 includes a plurality of drives 80 coupled to cylinders 82 that are each coupled to an individual driving fluid tube 42 and through the coupler 36 to a port 50 under a specific portion of the elastic sleeve 34. Within each cylinder 82 is a piston 84 and a quantity of a driving fluid 86. In certain embodiments, the driving fluid 86 is a gas. In certain embodiments, the driving fluid 86 is air. In certain embodiments, the driving fluid 86 is a liquid. In certain embodiments, the driving fluid 86 is water. In certain embodiments, the driving fluid 86 is a medical fluid such as normal saline (0.9% sodium chloride in sterile water). It is advantageous for the driving fluid 86 to be biocompatible such that any leakage or contamination by the driving fluid 86 of the medical fluid in container 14 that is being delivered to the patient 12 is not harmful to the patient 12. The drives are controlled by a processor 92 that receives signals from pressure sensors 90 through sensor electronics 94 and from an operator interface 96.

In this embodiment, each drive 80 is individually controlled to advance and retract the related piston 84. As a piston 84 advances, driving fluid 86 is forced through the driving fluid tubes 42 through coupler 36 and into internal passages 52 (of FIG. 3B, not visible in FIG. 9A) of support element 32 and out through port 50 into the space between the support element 32 and the portion of the elastic sleeve 34 that is over the port 50. The introduction of fluid into this space expands the portion of the elastic sleeve 34 until the elastic sleeve 34 contacts the internal surface of the bore 14 of outer shell 30, circumferentially blocking the flow path 54. When the drive 80 retracts the piston 84, the driving fluid 86 is withdrawn from the space between the support element 32 and the elastic sleeve 34, allowing the elastic sleeve 34 to contract and pull away from the internal surface of bore 14, opening the flow path 54. The illustrated embodiment of the IV pump 40 also includes pressure sensors 90 to monitor the pressure of the driving fluid 86 and position encoders 98 that send signals to the processor 92 such that the amount of driving fluid 86 displaced by each piston 84 is controlled. The IV pump 40 also includes vents 88 that are used to bleed air out of the driving fluid tubes 42 upon first connection between the IV pump 40 and the tubular pumping element 10 when a liquid drive fluid is used. The operation of the pumping system 16 is described relative to FIGS. 10A-10F. In certain embodiments, the cylinders 82 and driving fluid lines 42 are integral to the tubular pumping element 10 are discarded after use, wherein the cylinders 82 are detachably coupled to the drives 80.

Figure 9B:
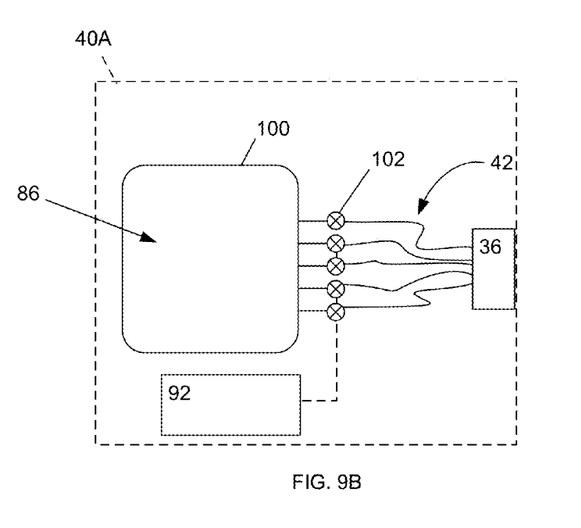
FIG. 9B is a schematic of a pressure-driven IV pump according to certain aspects of the disclosure.

FIG. 9B is a schematic of a pressure-driven IV pump 40A according to certain aspects of the disclosure. Not all elements of the IV pump 40 of FIG. 9A are repeated in FIG. 9B. In this embodiment, the driving fluid 86 is provided from a pressurized source 100 containing driving fluid 86 that is selectively connected through a plurality of valves 102 to the driving fluid tubes 42. The valves 60A, 60B of the tubular pumping element 10 are closed by application of a fixed pressure of the driving fluid 86 that is sufficient to expand the elastic sleeve 34 into contact with the outer shell 30. In certain embodiments, the pumping element 62 and compensator 64 are expanded by the providing the driving fluid 86 at a pressure slightly above the pressure of the damper 66. In certain embodiments, the pumping element 62 and compensator 64 are expanded by providing the driving fluid 86 at an increasing pressure of the duration of the delivery and fill strokes, respectively. In certain embodiments, the pumping element 62 and compensator 64 are collapsed by controlling the pressure in the respective pumping elements 62, 64 to be slightly less than the pressure of the damper 66. In certain embodiments, the pumping element 62 and compensator 64 are collapsed decreasing the pressure in the respective pumping elements 62, 64 over the duration of the fill and delivery strokes, respectively.

Figure 10A:
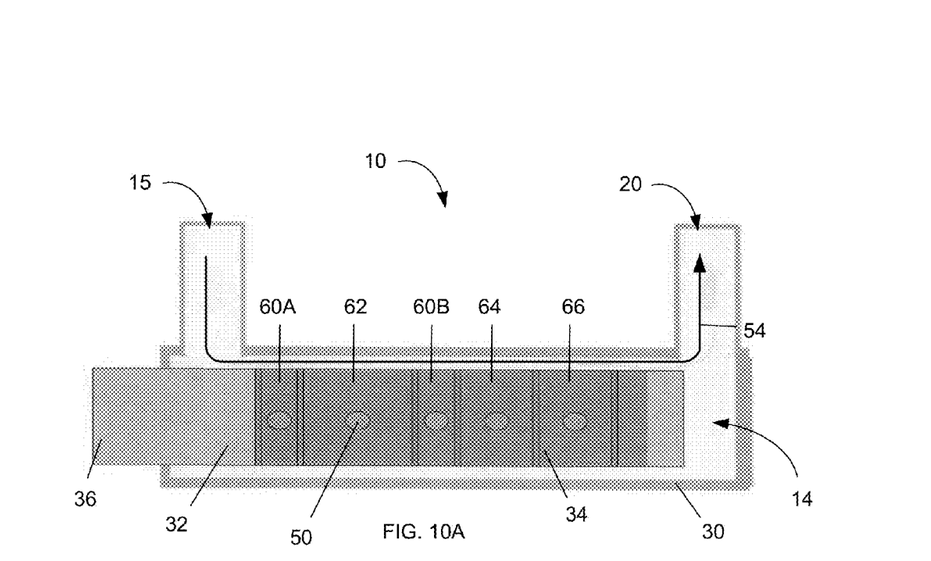
FIGS. 10A-10F depict sequential configurations of the tubular pumping element during operation according to certain aspects of the disclosure.

FIGS. 10A-10F depict sequential configurations of the tubular pumping element 10 during operation according to certain aspects of the disclosure. FIG. 10A depicts the configuration of tubular pumping element 10 when the IV pump 40 (not shown) and IV set 46 (not shown) are first connected to patient 12 (not shown) and the container 14 (not shown) of medical fluid. In the embodiment of the tubular pumping element 10 depicted in FIGS. 10A-10F, portions 60A and 60B are valves, portion 62 is the pumping element, portion 64 is a compensation element, and portion 66 is a damper and subsequent discussion of FIGS. 10A-10F will refer to them with these names. In this configuration, the flow path 54 is primed by venting the IV set 46 at the outlet 20 such that medical fluid is drawn from the container 44 through the inlet 15 to fill the bore 14 of the tubular pumping element 10. As the driving fluid 86 of this embodiment is a liquid, the driving fluid tubes 42 (not shown) that are connected to coupler 36 and the internal channels 52 (not visible in FIG. 9) vented using the vents 88 of FIG. 9, allowing the driving fluid tubes 42 and internal channels 52 to be filled with the liquid driving fluid 86.

Figure 10B:
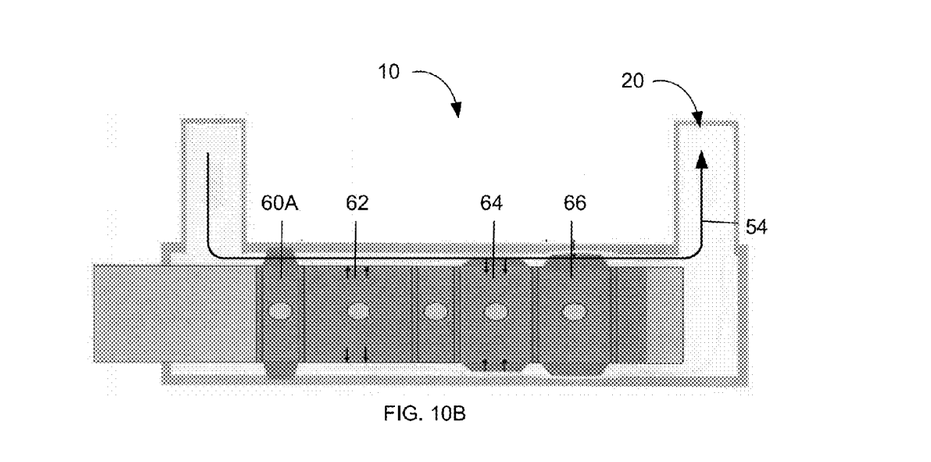

FIG. 10B depicts the configuration of tubular pumping element 10 at the start of the delivery stroke. Valve 60A is expanded thereby blocking the flow path 54. Damper 66 is expanded and being held at a fixed pressure that is less than the maximum pressure that can be delivered by the pumping element 62 or the compensator 64 but greater than the maximum backpressure that is expected at outlet 20. Variations within the pumping elements 62, 64 would compress or expand the elastic sleeve 34 in those areas, affecting the volumetric accuracy of the pumping. The damper 66 prevents fluctuations in backpressure from affecting the pumping elements 62, 64. When the pressure of the medical fluid over the pumping elements 62, 64 exceeds the pressure of the damper 66, as it does in normal operation, medical fluid will flow past the damper 66 and out the outlet 20. At the start of the delivery stroke, pumping element 62 is fully collapsed and starts expanding while compensator 64 is contracting. As compensator 64 is shorter than pumping element 62, the pumping element 62 is displacing more medical fluid than is needed to fill the space around the contracting compensator 64, and pressure of the medical fluid over the pumping elements 62, 64 rises to the level of the damper 66, whereupon the additional medical fluid passes by the damper 66 and out the outlet 20.

Figure 10C:
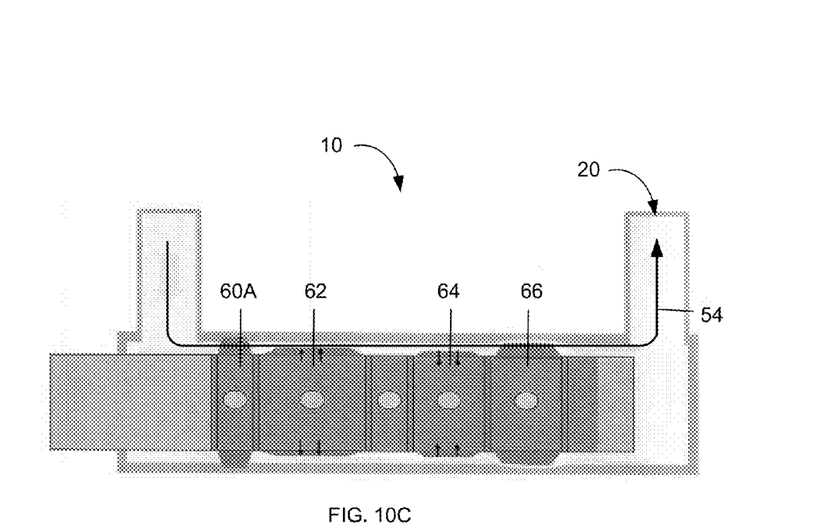

FIG. 10C depicts the configuration of tubular pumping element 10 during the delivery stroke. The pumping element 62 continues to expand while the compensator 64 continues to contract. Medical fluid is passing by the damper 66 at a constant rate and being delivered to the patient 12.

Figure 10D:
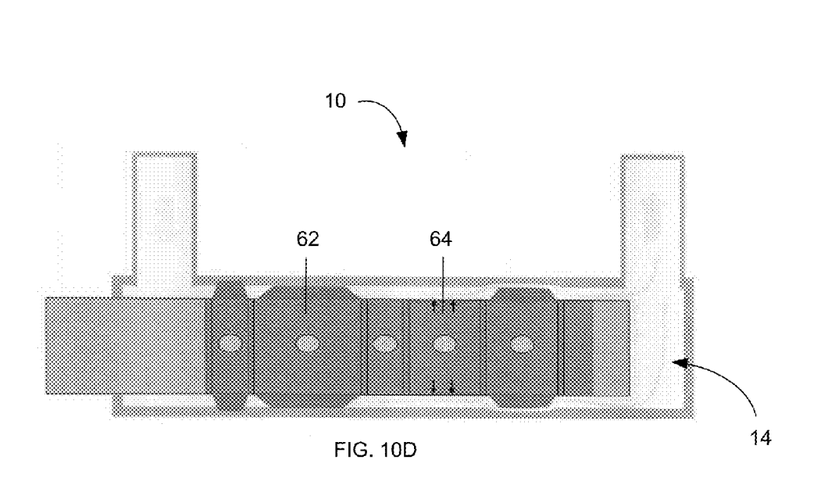

FIG. 10D depicts the configuration of tubular pumping element 10 at the completion of the delivery stroke. Pumping element 62 is fully expanded and compensator 64 is fully collapsed. In certain embodiments, the pumping element 62 is in contact with the internal wall of the bore 14 when fully expanded. Flow momentarily stops at this point in the operation of IV pump 40. In certain embodiments, the compensator 64 is in full contact with the support element 14 when fully collapsed. In certain embodiments, one or both of the pumping element 62 and compensator 64 do not contact the outer shell 30 in their fully expanded position. In certain embodiments, one or both of the pumping element 62 and compensator 64 and are not in contact with the support element 32 in their fully collapsed positions.

Figure 10E:
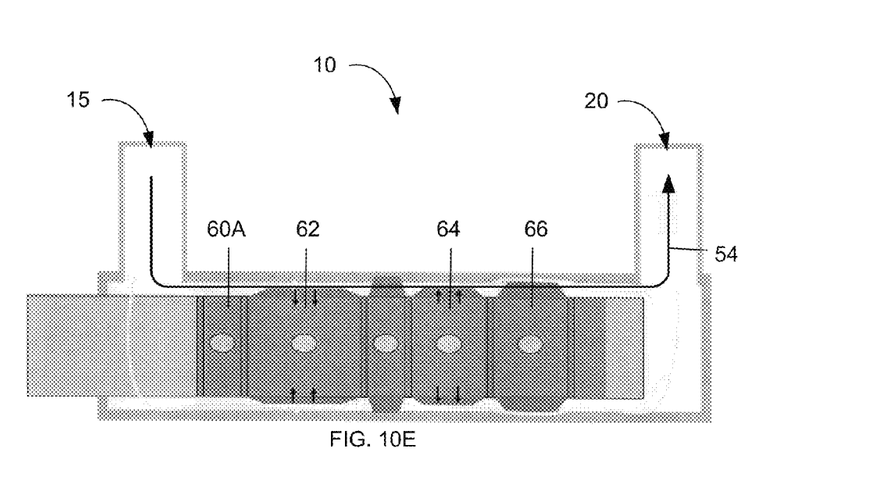

FIG. 10E depicts the configuration of tubular pumping element 10 at the start of the fill stroke, which occurs immediately after the tubular pumping element 10 completes the delivery stroke. Valve 60A is collapsed and valve 60B is expanded. Pumping element 62 is fully expanded and beings to contract, drawing fluid in through inlet 15 past the collapsed valve 60A. At the same time, compensator 64 is expanding and pushing fluid past damper 66 out through the outlet 20. In this manner, the delivery of medical fluid continues at the same rate and pressure as occurred during the delivery stroke.

Figure 10F:
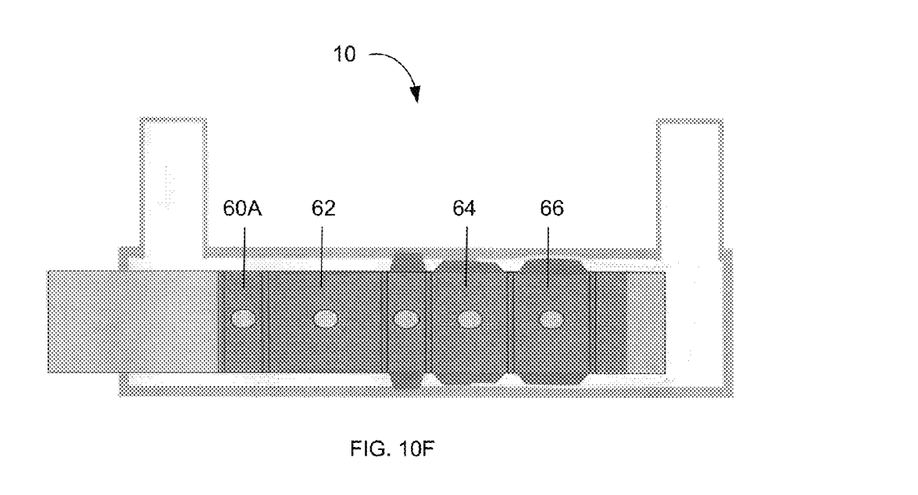

FIG. 10F depicts the configuration of tubular pumping element 10 at the completion of the fill stroke. The pumping element 62 is fully collapsed. The compensator 64 is fully expanded. Flow momentarily stops at this point in the operation of IV pump 40. The IV pump 40 inflates valve 60A and deflates valve 60B to return to the configuration of FIG. 10B and start the next delivery stroke. The IV pump 40 continues the sequence of delivery and fill strokes as shown in FIGS. 10B-10F to provide near-continuous fluid delivery to the patient at a constant flow rate. While the pressure of the medical fluid over the pumping elements 62, 64 remains constant at the pressure of the damper 66, the pressure of the medical fluid drops after passing the damper 66 to the pressure required to deliver the fluid to the patient 12 at the designated rate.

Figure 11:
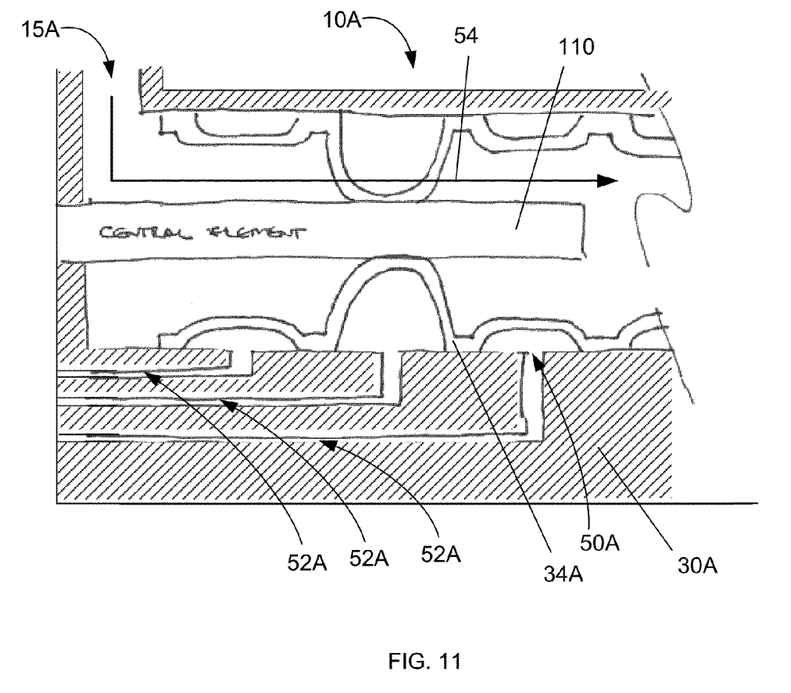
FIG. 11 depicts another embodiment of the tubular pumping element according to certain aspects of the disclosure.

FIG. 11 depicts an embodiment of the tubular pumping element 10A where the elastic sleeve 34A is located on the internal surface of an outer shell 30A and expands toward a central tube 110 and seals against the central tube 110 to block the toroidal flow path 54 according to certain aspects of the disclosure. In this embodiment, the flow passages 52A are in the outer shell 30A and connect to ports 50A in the internal surface of outer shell 30A. The sequence of operation of tubular pumping element 10A is essentially the same as for tubular pumping element 10.

In summary, the tubular pumping element described and claimed herein provides for the delivery of a fluid at a near-constant rate that is not affected by variations in backpressure at the outlet of the pumping system. The tubular pumping element is compact and quiet and provides a positive displacement of the delivered fluid. The drives and related components may be remotely located from the tubular pumping element, further quieting the operation of the pumping system in the proximity of the patient.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A tubular pumping element for pumping a liquid, the tubular pumping element comprising:

an outer shell comprising: a bore having an inlet and an outlet at opposite ends of the bore; and a flow path for the liquid from the inlet through the bore to the outlet;
a support element located within the bore of the outer shell;
an elastic sleeve over the support element; the elastic sleeve comprising a plurality of expandable portions;
wherein the support element further comprises a plurality of fluid passages each coupled to a respective port on the surface of the support element under a proximate one of the plurality of expandable portions of the elastic sleeve; and
wherein introduction of a driving fluid into one of the fluid passages causes the expandable portion of the elastic sleeve that is proximate to the respective port to expand.

2. The tubular pumping element of claim 1, wherein the elastic sleeve has at least one valve portion, wherein the valve portion expands to circumferentially contact the outer shell and block the flow path through the bore.

3. The tubular pumping element of claim 2, wherein the elastic sleeve has a pumping portion and a compensation portion, wherein the pumping portion expands and contracts to pump the liquid out of the outlet and the compensation portion expands while the pumping portion is contracting to maintain the flow of the liquid out of the outlet.

4. The tubular pumping element of claim 3, wherein the elastic sleeve has a damper portion that is maintained at a constant pressure that is higher than a maximum backpressure at the outlet and lower than a maximum pumping pressure created when the pumping and compensation portions expand.

5. The tubular pumping element of claim 4, wherein the order of the portions of the elastic sleeve along the flow path from the inlet to the outlet is a first valve portion, the pumping portion, a second valve portion, the compensation portion, and the damper.

6. The tubular pumping element of claim 3, wherein the pumping portion has a length along the flow path that is greater than the compensation portion.

7. The tubular pumping element of claim 3, wherein the pumping portion has a length along the flow path that is equal to the compensation portion.

8. An intravenous (IV) set for use with an infusion pump to deliver a medical fluid from a source of medical fluid to a patient, the IV set comprising:

a tubular pumping element comprising:
an outer shell comprising a bore and a flow path for the medical fluid from an inlet through the bore to an outlet;
a support element located within the bore of the outer cylinder; and
an elastic sleeve over the support element; the elastic sleeve comprising a plurality of expandable portions;
wherein the support element further comprises a plurality of separate fluid passages each coupled to a port on the surface of the support element under one of the plurality of expandable portions of the elastic sleeve; and
wherein introduction of a driving fluid into one of the fluid passages causes the expandable portion of the elastic sleeve that is proximate to the respective port to expand;
a first tube having first and second ends, the first end coupled to the inlet of the outer shell, the second end configured to couple to source of medical fluid; and
a second tube having first and second ends, the first end coupled to the outlet of the outer shell, the second end configured to couple to a cannula adapted to introduce medical fluid into the body of the patient.

9. The IV set of claim 8, wherein the elastic sleeve has at least one valve portion, wherein the valve portion expands to contact the outer shell and block the flow path.

10. The IV set of claim 9, wherein the elastic sleeve has a pumping portion and a compensation portion, wherein the pumping portion expands and contracts to pump the medical fluid out of the outlet and the compensation portion expands while the pumping portion is contracting to maintain the flow of the medical fluid out of the outlet.

11. The IV set of claim 10, wherein the elastic sleeve has a damper portion that is maintained at a constant pressure that is higher than a maximum backpressure at the outlet and lower than a maximum pumping pressure created when the pumping and compensation portions expand.

12. The IV set of claim 11, wherein the order of the portions of the elastic sleeve along the flow path from the inlet to the outlet is a first valve portion, the pumping portion, a second valve portion, the compensation portion, and the damper.

13. The IV set of claim 10, wherein the pumping portion has a length along the flow path that is greater than the compensation portion.

14. The IV set of claim 10, wherein the pumping portion has a length along the flow path that is equal to the compensation portion.

15. The pump system of claim 9, further comprising a plurality of cylinders containing driving fluid and having pistons that are each coupled to a drive that advances and retracts the piston under control of a controller, wherein each cylinder is coupled to one of the fluid passages such that advancement of the piston introduces driving fluid into the fluid passage and thereby expands the portion of the elastic sleeve that is proximate to the port coupled to the driving fluid connector.

16. A pump system for delivery of medical fluid from a source of medical fluid to a patient, the pump system comprising:
    an IV set comprising:
        a tubular pumping element comprising:
            an outer shell comprising a bore and a flow path for the medical fluid from an inlet through the bore to an outlet;
            a support element located within the bore of the outer cylinder; and
            an elastic sleeve over the support element; the elastic sleeve comprising a plurality of expandable portions;
            wherein the support element further comprises a plurality of separate fluid passages each coupled to a port on the surface of the support element under one of the plurality of expandable portions of the elastic sleeve; and
            wherein introduction of a driving fluid into one of the fluid passages causes the expandable portion of the elastic sleeve that is proximate to the respective port to expand;
        a first tube having first and second ends, the first end coupled to the inlet of the outer shell, the second end configured to couple to the source of medical fluid; and
        a second tube having first and second ends, the first end coupled to the outlet of the outer shell, the second end configured to couple to a cannula adapted to introduce medical fluid into the body of the patient; and
    an infusion pump comprising a source of driving fluid coupled to the fluid passages of the support element and configured to introduce and extract drive fluid from the fluid passages so as to expand and contract the expandable portions of the elastic sleeve.

17. The pump system of claim 16, wherein the elastic sleeve has at least one valve portion, wherein the valve portion expands to contact the outer shell and block the flow path.

18. The pump system of claim 17, wherein the elastic sleeve has a pumping portion and a compensation portion, wherein the pumping portion expands and contracts to pump the medical fluid out of the outlet and the compensation portion expands while the pumping portion is contracting to maintain the flow of the medical fluid out of the outlet.

19. The tubular pumping element of claim 18, wherein the driving fluid is a liquid.

20. The tubular pumping element of claim 19, wherein the driving fluid is a medical fluid.

21. The tubular pumping element of claim 20, wherein the driving fluid is a saline solution.

22. The pump system of claim 18, wherein the elastic sleeve has a damper portion that is maintained at a constant pressure that is higher than a maximum backpressure at the outlet and lower than a maximum pumping pressure created when the pumping and compensation portions expand.

23. The pump system of claim 22, wherein the order of the portions of the elastic sleeve along the flow path from the inlet to the outlet is a first valve portion, the pumping portion, a second valve portion, the compensation portion, and the damper.

24. The tubular pumping element of claim 18, wherein the pumping portion has a length along the flow path that is greater than the compensation portion.

25. The tubular pumping element of claim 18, wherein the pumping portion has a length along the flow path that is equal to the compensation portion.

26. The tubular pumping element of claim 18, wherein the driving fluid is a gas.

27. The tubular pumping element of claim 18, wherein the driving fluid is air.

* * * * *